(12) United States Patent
Vogt et al.

(10) Patent No.: US 8,012,173 B2
(45) Date of Patent: Sep. 6, 2011

(54) SURGICAL SUTURE MATERIAL WITH AN ANTIMICROBIAL SURFACE AND PROCESS FOR PROVIDING AN ANTIMICROBIAL COATING ON SURGICAL SUTURE MATERIAL

(75) Inventors: Sebastian Vogt, Erfurt (DE);
Klaus-Dieter Kuhn, Marburg-Elnhausen (DE); Hubert Büchner, Nümberg (DE)

(73) Assignee: Heraeus Kulzer GmbH, Hanau (DE)

( * ) Notice: Subject to any disclaimer, the term of this patent is extended or adjusted under 35 U.S.C. 154(b) by 0 days.

(21) Appl. No.: 12/889,550

(22) Filed: Sep. 24, 2010

(65) Prior Publication Data

US 2011/0015673 A1 Jan. 20, 2011

Related U.S. Application Data

(62) Division of application No. 11/877,846, filed on Oct. 24, 2007, now Pat. No. 7,829,133.

(30) Foreign Application Priority Data

Oct. 25, 2006 (DE) .......................... 10 2006 051 093

(51) Int. Cl.
*A61B 17/04* (2006.01)
(52) U.S. Cl. ..... 606/228; 427/2.1; 427/2.31; 427/434.2; 427/434.6; 427/434.7
(58) Field of Classification Search .................... 606/228
See application file for complete search history.

(56) References Cited

U.S. PATENT DOCUMENTS

| 2004/0092588 A1* | 5/2004 | Kramer et al. ................. 514/554 |
| 2005/0124725 A1 | 6/2005 | Modak et al. |

FOREIGN PATENT DOCUMENTS

| DE | 26 38 831 | 10/1977 |
| DE | 27 55 344 | 6/1978 |
| DE | 689 07 080 | 9/1993 |
| DE | 101 09 925 A1 | 9/2002 |
| EP | 1669093 | 6/2006 |
| GB | 1090421 | 11/1967 |
| JP | 10 511024 A | 10/1998 |
| JP | 2006 152306 A | 6/2006 |
| WO | 0057933 | 10/2000 |
| WO | 02069874 | 9/2002 |
| WO | 2004 108854 A1 | 12/2004 |
| WO | 2005072281 | 8/2005 |

OTHER PUBLICATIONS

Bartoszewicz, Marzenna, Prace Oryginalne, "Biofilm jako podstawowy mechanizm zakzenia miejsca operowanego—metody prewencji w leczeniu miejscowym", Chirugia Polska 2006, 8, 3, 171-178.

Storch, Mark L., "Experimental Efficacy Study of Coated VICRYL plus Antibacterial Suture in Guinea Pigs Challenged with *Staphylococcus aureus*", Surgical Infections, vol. 5, No. 3, 2004, 281-288.

* cited by examiner

*Primary Examiner* — Dah-Wei Yuan
*Assistant Examiner* — Andrew Bowman
(74) *Attorney, Agent, or Firm* — Norris McLaughlin & Marcus, P.A.

(57) ABSTRACT

A surgical suture material with an antimicrobial surface is described, the surface exhibiting a coating containing a) at least one fatty acid, b) octenidine dichloride and/or dequalinium chloride and c) optionally oligomeric lactic acid esters. In addition, a process for coating surgical suture material is described which is characterized by the fact that the thread material is wetted with a homogeneous methanolic solution of octenidine dichloride and/or dequalinium chloride and subsequently the methanol is evaporated, a coating forming on the thread surface.

4 Claims, No Drawings

SURGICAL SUTURE MATERIAL WITH AN ANTIMICROBIAL SURFACE AND PROCESS FOR PROVIDING AN ANTIMICROBIAL COATING ON SURGICAL SUTURE MATERIAL

This application is a division of U.S. patent application Ser. No. 11/877,846, filed Oct. 24, 2007, now allowed, which claims foreign priority benefit under 35 U.S.C. §119 of the German Patent Application No. 10 2006 51 093.3 filed Oct. 25, 2006.

The present invention relates to a surgical suture material with an antimicrobial surface and to a process for providing an antimicrobial surface on a surgical suture material.

Surgical suture material can be divided into monofilament and polyfilament threads on the basis of its construction. Polyfilament threads can exhibit a so-called wicking effect. This means that tissue fluid migrates along the thread as a result of capillary action. It is possible for a migration of microbial germs to be associated therewith such that infections may spread along the thread material. It is therefore desirable to provide surgical suture material with a finish in such a way that settling of germs on the thread surface and thus a migration of germs along the thread is effectively prevented.

In the case of resorbable suture materials, polyfilament, braided polyglycolide threads are of particular practical importance. So far, only one polyglycolide-based thread material, marketed by Ethicon, which is coated with the antiseptic triclosan has been available on the market. This antiseptic is a chlorinated biphenyl derivative which has an antiseptic effect on gram-positive bacteria. However, a thread material with a much wider antibacterial effectiveness covering also gram-negative bacteria, yeasts and fungi would be desirable. Polyfilament threads are also commonly used for the group of non-resorbable thread materials. Thus, polyfilament surgical steel wire is used in thorax surgery, for example. At present, no commercially marketed non-resorbable suture materials with an antimicrobial finish are known.

Numerous antiseptically effective substances have been known for decades and are in use in the medical field. Apart from water-soluble chlorohexidine salts for dental care, octenidine dichloride solutions sold by Schüle & Mayr under the trade name Octenisept® are widely used in surgery for wound disinfection and surface disinfection. Octenisept is an aqueous alcoholic solution of octenidine dichloride and phenoxyethanol. Octenidine dichloride ((1,1'-(1,10-decane diyl) bis[4-(octylamino)pyridinium] dichloride) is characterized, in comparison with other cationic antiseptics, by the fact that it is doubly positively charged. Octenidine dichloride has a very wide spectrum of activity and comprises gram-positive and gram-negative bacteria as well as yeasts and fungi. It was developed by Sterling Inc. in 1977.

Dequalinium chloride has a similar structure with, again, two cationic centers. Dequalinium chloride (1,10-decamethylene bis(4-amino-2-methyl quinolinium) dichloride) was described by Allen & Hanburys in 1957.

Both octenidine dichloride and dequalinium chloride are characterized by a very broad spectrum of activity and a good tolerance with respect to soft tissue, in particular the mucous membrane. Correspondingly, preparations containing octenidine dichloride, for example, have been described for wound and mucous membrane disinfection (DE 101 09 925 A1). However, octenidine dichloride and dequalinium chloride do not exhibit any marked adhesion effect on the surface of common suture material.

The invention is based on the object of developing a surgical suture material which is finished in such a way that it is protected from being colonized by microbes and that the antimicrobial protection covers a wide spectrum of germs. Moreover, an uncomplicated process is to be developed which permits an antimicrobial surface to be applied onto commercial suture material. The process is to be designed in such a way that the suture material is not negatively affected in terms of its structure by the coating process.

Surprisingly enough, it has been found that, by adding at least one fatty acid, it has been possible to cause octenidine dichloride and also dequalinium chloride to adhere to the surfaces of suture material. The antiseptics octenidine dichloride and dequalinium chloride can be applied onto the surfaces of surgical suture material together with the fatty acid(s) acting as adhesion promoter. It follows from this that a coating consisting of a mixture of at least one fatty acid and octenidine dichloride and/or dequalinium chloride is applied onto the surface of the thread.

Preferred fatty acids are lauric acid, palmitic acid and stearic acid. The fatty acids need not necessarily be used as pure substances. It is also possible to use fatty acids contaminated by monofatty acid glycerides, difatty acid glycerides and trifatty acid glycerides. In addition, it is possible to use mixtures of fatty acids and oligomeric lactic acid esters. The weight ratio of octenidine dichloride or dequalinium chloride to fatty acid is preferably 1:0.1 g to 1:5, particularly preferably 1:1.

The object of the invention is also achieved by a process for coating surgical suture material in the case of which the material is wetted with a homogeneous methanolic solution of octenidine dichloride and/or dequalinium chloride and at least one fatty acid and the methanol is subsequently evaporated, a coating being formed on the thread surface. It is also possible to use mixtures of methanol and other low alcohols such as ethanol, propanol and isopropanol instead of methanol. The advantage of using methanolic solutions is that commonly used polyglycolide threads, polydioxanone threads and poly-epsilon caprolactone co-L-lactide threads are not caused to swell up by the short-term action of methanol and, consequently, the thread structure remains intact.

The invention is illustrated in further detail by the following examples without these limiting the invention.

EXAMPLE 1

300 mg of dequalinium chloride (Solmag) and 300 mg of palmitic acid (Fluka) are dissolved in 28.800 g of methanol (Fluka) at room temperature. A clear solution is formed. A piece of braided polyglycolide thread 50 cm in length (USP 2.0) is immersed into this solution. Subsequently, the methanol is allowed to evaporate at room temperature. The coating mass is determined gravimetrically. The coating mass is 0.6 mg.

EXAMPLE 2

600 mg of octenidine dichloride (Dishman Pharmaceuticals) and 600 mg of palmitic acid (Fluka) are dissolved in 28.800 g of methanol (Fluka) at room temperature. A clear solution is formed. A piece of braided polyglycolide thread 50 cm in length (USP 2.0) is immersed into this solution. Subsequently, the methanol is allowed to evaporate at room temperature. The coating mass is determined gravimetrically. The coating mass is 1.4 mg.

What is claimed is:

1. Surgical suture material comprising an antimicrobial surface, wherein the surface exhibits a coating comprising the following components:
   a) at least one fatty acid,
   b) at least one of octenidine dichloride and dequalinium chloride, and
   c) optionally oligomeric lactic acid esters.

2. Surgical suture material according to claim 1, wherein the at least one fatty acid is selected from the group consisting of lauric acid, palmitic acid and stearic acid.

3. Surgical suture material according to claim 1, wherein the weight ratio of component b) to component a) is 1.0:0.1 to 1.0:5.0.

4. Surgical suture material according to claim 3, wherein the weight ratio is 1.0:1.0.

* * * * *